United States Patent
Alas et al.

(10) Patent No.: US 6,403,834 B1
(45) Date of Patent: Jun. 11, 2002

(54) METHOD FOR PREPARING TRIS(ETHER-AMINE)

(75) Inventors: Michel Alas, Melle; Albert Bouniot, Paizay Le Tort, both of (FR)

(73) Assignee: Rhodia Chimie, Billancourt Cedex (FR)

( * ) Notice: Subject to any disclaimer, the term of this patent is extended or adjusted under 35 U.S.C. 154(b) by 0 days.

(21) Appl. No.: 09/831,401

(22) PCT Filed: Nov. 9, 1999

(86) PCT No.: PCT/FR99/02745

§ 371 (c)(1),
(2), (4) Date: Jul. 23, 2001

(87) PCT Pub. No.: WO00/27796

PCT Pub. Date: May 18, 2000

(30) Foreign Application Priority Data

Nov. 9, 1998 (FR) .............................................. 98 14081

(51) Int. Cl.$^7$ ...................... C07C 209/16; C07C 213/02
(52) U.S. Cl. ...................... 564/399; 564/401; 564/402; 564/445; 564/447; 564/474; 564/475; 564/478
(58) Field of Search ................................ 564/399, 401, 564/402, 445, 447, 474, 475, 478

(56) References Cited

U.S. PATENT DOCUMENTS 2,285,419 A    6/1942  Dickey et al.
4,408,075 A  * 10/1983  Soula et al. ................ 564/474

FOREIGN PATENT DOCUMENTS

EP    0 005 094     10/1979
EP    0 018 884     11/1980
WO    WO 88 06579    9/1988

OTHER PUBLICATIONS

Gerard Soula, "Tris(polyoxaalkyl)amines (Trident), a New Class of Solid–Liquid Phase–Transfer Catalysts", Journal of Organic Chemistry, vol. 50, No. 20, 1985, pp. 3717–3721, XP–002105964.

* cited by examiner

*Primary Examiner*—Brian J. Davis
(74) *Attorney, Agent, or Firm*—Burns, Doane, Swecker & Mathis, LLP

(57) ABSTRACT

The invention concerns a method for preparing tris(ether-amines) of formula (I): $N[A—O—(B—O)_n—R]_3$ wherein R, A, B and n are as defined in Claim 1, comprising the reaction, in liquid phase, of an alkylene-glycol monoether of formula (II): $HO—A—O—(B—O)_nR$ wherein R, A, B and n are as defined in Claim 1, with an ammonolysis agent selected among ammonia and an etheramine of formula (I'): $H_{3-p}N[A—O—(B—O)_nR]_p$ wherein: A, B, n and R are as defined in Claim 1 and p represent 1 or 2, at a temperature ranging between 100 and 250° C., by contacting reagents with a hydrogenation-dehydrogenation catalyst.

15 Claims, No Drawings

METHOD FOR PREPARING TRIS(ETHER-AMINE)

This application is a 371 of PCT/FR99/02795 filed Nov. 9, 1999.

The present invention relates to an improved process for preparing tertiary amines which can be used as sequestering agents for solubilising organic or inorganic metal salts in organic solvents. These tertiary amines may also be used as emulsifiers.

The tertiary amines prepared by the process according to the invention have the general formula (I):

$$N[A-O-(B-O)_n-R]_3 \qquad (I)$$

wherein:

R denotes an alkyl radical having 1 to 24 carbon atoms, optionally substituted by one or more $C_{1-12}$-alkoxy radicals; a saturated carbocyclic, monocyclic or polycyclic radical having 3 to 10 carbon atoms, optionally substituted by one or more $C_{1-12}$-alkoxy radicals; an alkyl radical having 1 to 12 carbon atoms and carrying a saturated carbocyclic, monocyclic or polycyclic group having 3 to 10 carbon atoms, the alkyl part optionally being substituted by one or more $C_{1-12}$-alkoxy radicals and the saturated carbocyclic group optionally being substituted by one or more $C_{1-12}$-alkyl groups or $C_{1-12}$-alkoxy groups; an aromatic carbocyclic, monocyclic or polycyclic radical having 6 to 22 carbon atoms and optionally substituted by one or more $C_{1-12}$-alkoxy or $C_{1-12}$-alkyl groups; and an alkyl radical having 1 to 12 carbon atoms and carrying an aromatic carbocyclic, monocyclic or polycyclic group having 6 to 18 carbon atoms, the alkyl part optionally being substituted by one or more $C_{1-12}$-alkoxy groups and the aromatic group optionally being substituted by one or more $C_{1-12}$-alkyl groups or $C_{1-12}$-alkoxy groups; p A and B, which may be identical or different, independently denote a straight alkylene chain having 1 to 24 carbon atoms optionally substituted by one or more groups selected from among $C_{1-12}$-alkyl and $C_{1-12}$-alkoxy; and n denotes from 0 to 12.

The value of amines of this kind is the subject matter of French Patent Application 79 05438.

Numerous preparation processes have been described in the art for preparing tertiary amines of this kind. Reference may be made, for example, to EP161459, EP5094, EP18884 and the work by Pétrov which appeared in Zh. Obsch. Khim (1970), 40(7), 1611–1616.

However, the methods described have two serious drawbacks: the yields are low and the products are difficult to purify.

From the point of view of the yields obtained, the method of synthesis described in EP18884 is particularly advantageous. It consists in using ammonolysis, in liquid phase, of an alkyleneglycol monoether of formula F1:

$$HO-A-O-(B-O)_n-R \qquad F1$$

wherein:

R denotes $(C_{1-24})$alkyl, cyclohexyl, phenyl or $(C_{1-12})$ alkylphenyl;

A and B, which may be identical or different, independently represent a straight alkylene chain $(C_{2-3})$ in which the carbon atoms are optionally substituted by methyl or ethyl; and n denotes an in between 0 and 4;

in the presence of a hydrogenation/dehydrogenation catalyst at between 100 and 250° C., the ammonolysis operation being carried out by contacting the ammonolysis agent or agents with a mixture consisting of the above-mentioned alkyleneglycol monoether and the catalyst.

According to this publication, the ammonolysis agents are selected from ammonia and the ether-amines of formula F2:

$$H_{3-p}N[A-O(B-O)_n-R]_p \qquad F2$$

wherein:

R denotes $(C_{1-24})$alkyl, cyclohexyl, phenyl or $(C_{1-12})$ alkylphenyl;

A and B, which may be identical or different, independently denote a straight $(C_{2-3})$alkylene chain wherein the carbon atoms are optionally substituted by methyl or ethyl; and n denotes an integer between 0 and 4; and p is an integer equal to 1 to 2.

In spite of the low cost of the raw materials, this process is not economical. At the end of the reaction, the reaction medium is separated from the catalyst by filtration. In fact, the operation of filtration is not easy and requires special filtration equipment which is expensive both to buy and maintain, as the hydrogenation/dehydrogenation catalyst is pyrophoric and abrasive.

Furthermore, the elimination of the catalyst is a laborious task which is frequently incomplete. Thus, there is a substantial reduction in the yield in as much as traces of catalyst in the crude tertiary amine cause it to decompose during subsequent steps of purification by distillation.

Finally, the method according to the prior art is not well suited to industrialisation of the process as it would require the use of excessive quantities of catalyst, which is particularly expensive.

The process according to the invention sets out to overcome the disadvantages of the prior art process.

More precisely, the invention relates to a process for preparing tris(ether-amines) of formula (I) as defined hereinbefore comprising reacting, in liquid phase, an alkyleneglycol monoether of formula (II):

$$HO-A-O-(B-O)_n-R \qquad (II)$$

wherein:

R denotes an alkyl radical having 1 to 24 carbon atoms, optionally substituted by one or more $C_{1-12}$-alkoxy radicals; a saturated carbocyclic, monocyclic or polycyclic radical having 3 to 10 carbon atoms, optionally substituted by one or more $C_{1-12}$-alkoxy radicals; an alkyl radical having 1 to 12 carbon atoms and carrying a saturated carbocyclic, monocyclic or polycyclic group having 3 to 10 carbon atoms, the alkyl part optionally being substituted by one or more $C_{1-12}$-alkoxy radicals and the saturated carbocyclic group optionally being substituted by one or more $C_{1-12}$-alkyl groups or $C_{1-12}$-alkoxy groups; an aromatic carbocyclic, monocyclic or polycyclic radical having 6 to 22 carbon atoms and optionally substituted by one or more $C_{1-12}$-alkoxy or $C_{1-12}$-alkyl groups; and an alkyl radical having 1 to 12 carbon atoms and carrying an aromatic carbocyclic, monocyclic or polycyclic group having 6 to 18 carbon atoms, the alkyl part optionally being substituted by one or more $C_{1-12}$-alkoxy groups and the aromatic group optionally being substituted by one or more $C_{1-12}$-alkyl groups or $C_{1-12}$-alkoxy groups;

A and B, which may be identical or different, independently denote a straight alkylene chain having 1 to 24 carbon atoms optionally substituted by one or more groups selected from among $C_{1-12}$-alkyl and $C_{1-12}$-alkoxy; and n denotes from 0 to 12;

with an ammonolysis agent selected from among ammonia and an ether-amine of formula (I'):

$$H_{3-p}N[A—O—(B—O)_n—R]_p \qquad (I')$$

wherein A, B, n and R are as hereinbefore defined for formula (I) and p denotes 1 or 2, at a temperature between 100 and 250° C. by contacting the reagents with a hydrogenation/dehydrogenation catalyst.

According to the invention, the term saturated carbocyclic, monocyclic or polycyclic radical denotes a radical made up of one or more cycloalkyl nuclei. When said saturated carbocyclic radical comprises a plurality of cycloalkyl nuclei, the latter form condensed or bridged structures, indicating that each cycloalkyl nucleus has at least two carbon atoms in common with at least one other cycloalkyl nucleus.

Examples of condensed structures include, in particular, perhydronaphthylene and perhydroindane.

Similarly, an example of a bridge structure is norbornane.

However, saturated monocyclic carbocyclic radicals of the $(C_{3-8})$cycloalkyl type are preferred, such as cyclopropyl, cyclobutyl, cyclopentyl, cyclohexyl, cycloheptyl or cyclooctyl.

Within the scope of the invention the alkyl radicals are straight-chained or branched. The preferred alkyl radicals are the $C_{1-10}$-alkyl radicals, better still $(C_{1-6})$alkyl, and especially methyl, ethyl, propyl, isopropyl, butyl, isobutyl, sec-butyl, tert-butyl, pentyl and hexyl.

The aromatic carbocyclic radicals are monocyclic or polycyclic.

The polycyclic aromatic carbocyclic radicals have condensed aromatic nuclei.

Of these, the preferred ones are the mono- and bicyclic aromatic carbocyclic radicals having 6 to 10 carbon atoms, such as phenyl or napthyl.

Special examples of alkyl radicals carrying an aromatic carbocyclic radical are the $(C_{6-10})$aryl-$(C_{1-12})$alkyl groups and more particularly the $(C_{6-10})$aryl-$(C_{1-6})$alkyl groups such as benzyl or naphthylmethyl.

Within the scope of the invention, the preferred definitions given above for the alkyl groups, the saturated or aromatic carbocyclic radicals remain the preferred definitions of these groups when the latter form an integral part of alkoxy or alkyl groups carrying a saturated or aromatic carbocyclic radical.

The process according to the invention is more particularly suited to the preparation of the following sub-groups of the compounds of formula I.

A first sub-group is made up of compounds of formula I wherein:

R denotes $(C_{1-6})$alkyl optionally substituted by $(C_{1-6})$alkoxy; $(C_{3-8})$cycloalkyl optionally substituted by one or more $(C_{1-6})$alkoxy groups; $(C_{6-10})$aryl optionally substituted by one or more $(C_{1-6})$alkoxy groups; $(C_{6-10})$aryl-$(C_{1-6})$alkyl wherein the alkyl part is optionally substituted by $(C_{1-6})$alkoxy and the aryl part is optionally substituted by $(C_{1-6})$alkyl or $(C_{1-6})$alkoxy; or $(C_{3-8})$cycloalkyl-$(C_{1-6})$alkyl wherein the alkyl part is optionally substituted by one or more $(C_{1-6})$alkoxy groups and the cycloalkyl part is optionally substituted by $(C_{1-6})$alkyl or $(C_{1-6})$alkoxy;

A and B, which may be identical or different, denote a straight $(C_{1-6})$alkylene chain optionally substituted by one or more $(C_{1-6})$alkyl or $(C_{1-6})$alkoxy groups; and n denotes 0 to 6.

A second group of preferred compounds comprises compounds of formula I wherein:

R denotes $(C_{1-24})$alkyl, cyclohexyl, phenyl or $(C_{1-12})$alkylphenyl;

A and B, which may be identical or different, independently represent a straight $(C_{2-3})$alkylene chain wherein the carbon atoms are optionally substituted by methyl or ethyl; and n denotes an integer between 0 and 4.

A third group of preferred compounds comprises compounds of formula I wherein:

R denotes $(C_{1-6})$alkyl, cyclohexyl, phenyl or $(C_{1-6})$alkylphenyl;

A and B, which may be identical or different, independently represent a straight $(C_{2-3})$alkylene chain wherein the carbon atoms are optionally substituted by methyl or ethyl, and n denotes an integer between 0 and 4.

The process according to the invention is characterised in that contacting is carried out by passing a solution of said reagents, previously heated to a temperature of 100 to 250° C., through a catalytic bed consisting of particles of said hydrogenation/dehydrogenation catalyst.

The reagents used in the process according to the invention are alkyleneglycol monoether of formula (II):

$$HO—A—O—(B—O)_n—R \qquad (II)$$

wherein A, B, n and R are as hereinbefore defined for formula (I) and the ammonolysis agent which is selected from ammonia and an ether-amine of formula (I'):

$$H_{3-p}N[A—O—(B—O)_n—R]_p$$

wherein A, B, n, R and p are as hereinbefore defined. According to the process of the invention, a solution of the reagents is prepared, which is then heated to a temperature between 100 and 250° C., preferably between 100 and 180° C.

When the ammonolysis agent is ammonia, this is dissolved in alkyleneglycol monoether of formula (II): this may easily be done by dissolving ammonia gas in a solution of alkyleneglycol monoether.

When the ammonolysis agent is the primary amine of formula $$H_2N[A—O(B—O)_n—R]$$

or the secondary amine of formula $$HN[A—O(B—O)_n—R]_2$$

wherein A, B, n and R are as hereinbefore defined, the solution of reagents is prepared simply by mixing the reagents together.

The preferred primary amines which may be used in the process according to the invention are selection from:

oxa-3-butylamine oxa-3-pentylamine oxa-3-hexylamine oxa-3-heptylamine dioxa-3,6-heptylamine trioxa-3,6,9-undecylamine dioxa-3,6-octylamine trioxa-3,6,9-dodecylamine dioxa-3,6-nonylamine trioxa-3,6,9-tridecylamine dioxa-3,6-decylamine trioxa-3,6,9-tetradecylamine
phenoxy-5-oxa-3-pentylamine
phenoxy-8-dioxa-3,6-octylamine
cyclohexoxy-5-oxa-3-pentylamine
cyclohexoxy-8-dioxa-3,6-octylamine
nonylphenoxy-5-oxa-3-pentylamine
nonylphenoxy-8-dioxa-3,6-octylamine
dodecylphenoxy-5-oxa-3-pentylamine
dodecylphenoxy-8-dioxa-3,6-octylamine
dioxa-3,6-methyl-4-heptylamine
dioxa-3,6-dimethyl-2,4-heptylamine.

The preferred secondary amines which may be used in the process according to the invention are selected from among:
aza-5-dioxa-2,8-nonane
aza-8-tetraoxa-2,5,11,14-pentadecane
aza-11-hexaoxa-2,5,8,14,17,20-uneicosane
aza-6-dioxa-3,9-undecane
aza-10-tetraoxa-4,7,13,16-nonadecane
aza-9-tetraoxa-3,6,12,15-heptadecane
aza-12-hexaoxa-3,6,9,15,18,21-tricosane
aza-7-dioxa-4,10-tridecane
aza-13-hexaoxa-4,7,10,16,19,22-pentacosane
aza-8-dioxa-5,11-pentadecane
aza-11-tetraoxa-5,8,14,17-uneicosane
aza-14-hexaoxa-5,8,11,17,20,23-heptacosane
aza-6-oxa-3-phenoxy-1-undecane
aza-9-dioxa-3,6-phenoxy-1-heptadecane
aza-6-oxa-3-cyclohexoxy-1-undecane
aza-9-dioxa-3,6-cyclohexoxy-1-heptadecane
aza-6-oxa-3-nonylphenoxy-1-undecane
aza-9-dioxa-3,6-nonylphenoxy-1-heptadecane
aza-6-oxa-3-dodecylphenoxy-1-undecane
aza-9-dioxa-3,6-dodecylphenoxy-heptadecane
aza-8-tetraoxa-2,5,11,14-dimethyl-4,12-pentadecane, and
aza-8-tetraoxa-2,5,11,14-tetramethyl-4,6,10,12-pentadecane.

The reagent solution may contain, in addition to the above reagents, one or more solvents which are inert to the ammonolysis reaction.

Such solvents include, for example, aliphatic hydrocarbons, aromatic hydrocarbons or mixtures thereof, with a boiling point under atmospheric pressure of between 100 and 350° C.

The solution of reagents is then brought into contact with the catalyst by passing this solution through a catalytic bed consisting of said hydrogenation/dehydrogenation catalyst.

According to one embodiment of the invention, the solution of reagents is prepared beforehand upstream of the catalytic bed.

However, when the ammonolysis agent is ammonia, it is also possible to prepare the solution of reagents at the entrance to the catalytic bed by injecting a flow of ammonia gas into an incoming current of the solution of alkyleneglycol monoether.

The skilled person will readily be able to adjust the quantity of ammonolysis agent required to obtain the desired tertiary amine, depending on the reaction carried out.

Depending on the nature of the ammonolysis agent used, the reaction balance will vary.

When the ammonolysis agent is ammonia, the equation of the reaction balance is written as follows:

$$NH_3 + 3HO-A-O-(B-O)_n-R \rightarrow 3H_2O + N[A-O-(B-O)_n-R]_3 \quad (1)$$

When the ammonolysis agent is a primary amine of formula (I'), the equation of the reaction balance is written as follows:

$$NH_2[A-O-(B-O)_n-R] + 2HO-A-O-(B-O)_n-R \quad (2)$$
$$\rightarrow N[A-O-(B-O)_n-R]_3 + 2H_2O$$

When the ammonolysis agent is a secondary amine of formula (I'), the equation of the reaction balance is written as follows:

$$NH[A-O-(B-O)_n-R]_2 + 2HO-A-O-(B-O)_n-R \quad (3)$$
$$\rightarrow N[A-O-(B-O)_n-R]_3 + H_2O$$

Generally, the solution of reagents will contain 0.5 to 2 moles of ammonolysis agents per liter of alkyleneglycol monoether, preferably 1 to 2 moles/l.

When the solution of reagents is prepared by injecting ammonia gas into an incoming liquid current of a solution of alkyleneglycol monoether, at the entrance to the catalytic bed, the respective flow rates of gaseous ammonia and the alkyleneglycol monoether solution are regulated so as to prepare a solution of reagents containing about 0.5 mole to about 2 moles of ammonia per liter of alkyleneglycol monoether, preferably from 1 mole to 2 mol/l.

The catalytic bed consists of a layer of particles of a hydrogenation/dehydrogenation catalyst. The shape of the catalyst particles is not critical according to the invention provided that the layer of particles allows a liquid to pass through.

The catalyst particles may take the form of pellets, extruded material or optional porous granules or beads or platelets. Preferably, the equivalent mean diameter of the particles is between 3 mm to 15 mm. By equivalent mean diameter of the catalyst particles is meant the mean diameter in the case of particles in the form of solid beads, and the diameter of the solid bead of equivalent mass to that of the particle in the case of other types of particles.

Preferably, the specific surface area of the catalyst is between 2 and 200 m²/g.

The hydrogenation/dehydrogenation catalyst proper is of the same type as is used in EP Application 18884. These catalysts are based, for example, on nickel (0), cobalt (0), chromium (0) or a mixture of these metals. They contain a certain proportion of these same metals in a different state of oxidation so as to reduce their pyrophoric properties. Alternatively, the catalyst is based on a nickel oxide, a cobalt oxide, a chromium oxide or a mixture of these oxides. The catalyst may also contain one or more of the metal oxides defined above combined with nickel (0), cobalt (0) and/or chromium (0). The hydrogenation/dehydrogenation catalyst may be deposited on an inert support such as silica, magnesium oxide, aluminium, kieselguhr or titanium oxide. Catalysts containing copper cannot be used according to the invention.

Catalysts of this kind are currently commercially available. For example, there is the nickel-based catalyst Ni 563 sold by the company Procatalyse and the nickel-based catalysts Ni 3266 and Ni 5124 sold by Messrs. Harshaw Chemical Company. These catalysts are in the form of pellets (solid or hollow) which may be between 3 mm and 20 mm in diameter, as required. The apparent bulk density of these pellets is of the order of 1 to 1.5 tonnes/m³. The content of catalysing species is between 40 and 90% by weight, depending on the varieties. More precisely, the catalyst Ni 563 is a nickel-based catalyst deposited on a silica support. In this catalyst, the mass ratio Ni/(Ni+SiO$_2$) is about 80%. This catalyst is used in reduced form. In this form, the mass ratio of Ni/NiO is approximately 50/50, and this ratio can vary considerably without altering the performance of the catalyst.

Within the scope of the invention, nickel-based catalysts are preferred.

Preferably, the catalytic bed is kept in a vertical position, with the solution of reagent circulating from top to bottom or from bottom to top. Advantageously, the solution of reagents circulates from top to bottom. However, the arrangement of the catalytic bed and the direction of circulation of the solution within the catalytic bed are not critical according to the invention.

The dimensions of the catalytic bed should be adjusted depending on the desired production. However, the section of the catalytic bed perpendicular to the flow of liquid passing through the catalytic bed should not be so great that it prevents optimum contact between the catalyst and the flow of liquid. The optimum diameter of this section depends on the equivalent mean diameter of the catalyst and the flow rate of material to be treated. To calculate the optimum diameter the skilled person might for example refer to the "Chemical reactor omnibook of Levenspiel; OSU Book Stores Inc.".

According to the invention, the term spatial velocity denotes the ratio of the flow rate of the reagent solution expressed in tonnes/h to the total mass of the catalytic bed expressed in tonnes.

Advantageously, the spatial velocity is maintained at between 0.1 and 0.5 h$^{-1}$ when the equivalent diameter of the particles is between 3 and 15 mm.

According to a preferred embodiment of the invention, the catalytic bed is a tube lined with said particles of hydrogenation/dehydrogenation catalyst. Alternatively, it is possible to form the catalytic bed by arranging a number of lined tubes as defined above in a row.

The reaction of the ammonolysis agent with the alkyleneglycol monoether is preferably carried out at atmospheric pressure. However, it is possible to carry out the reaction under ammonia pressure or hydrogen pressure. Generally, the pressure will be maintained at between 1 and 15 atmospheres.

It is particularly advantageous to work in the presence of hydrogen while reacting the ammonolysis agent with the alkyleneglycol monoether, so as to extend the service life of the catalyst.

To do this, the catalytic bed is placed under hydrogen pressure or a current of hydrogen is passed through the catalytic bed while the solution of reagents is passing through the catalytic bed.

The process of the invention may be carried out continuously or semi-continuously.

A preferred method of operating continuously comprises continuously supplying the catalytic bed with a solution of the reagents which has previously been brought to a temperature of 100 to 250° C. (preferably 100 to 180° C.), recycling some of the solution leaving the catalytic bed into the entry to the catalytic bed or preferably into an intermediate position located between the entry and the exit of the catalytic bed.

Preferably, 50% to 70% of the solution leaving the catalytic bed is recycled into the head of the column.

When the work is carried out semi-continuously, the solution leaving the catalytic bed is recovered in a recovery tank which may or may not be fitted with a stirrer system, until the content of tri(ether-amine) of formula (I) is between 0.5 and 2 moles per liter in the recovery tank. When this concentration is reached, all the solution contained in the recovery tank is recycled back into the top of the catalytic bed and, in parallel, the supply of reagent solution to the catalytic bed is stopped. Depending on the desired degree of conversion of the alkyleneglycol monoether (II) into tris(ether-amine) of formula (I), the operation of recycling the recovered solution in the recovery tank may be repeated several times.

Thus, the invention also relates to a process comprising steps of:

(i) continuously supplying the catalytic bed with a solution of the reagents which has previously been heated to a temperature of 100 to 250° C. and recovering the treated solution at the exit from said catalytic bed in a recovery tank until a concentration of tris(ether-amine) of formula (I) of 0.5 to 2 mol/l is obtained in the recovery tank; then (ii) recycling the solution recovered in said recovery tank into the catalytic bed; and passing it through the catalytic bed once more, and (iii) repeating the step of recycling the solution recovered in the recovery tank, at the end of step (ii) into the catalytic bed as many times as is necessary to obtain the desired degree of conversion into tertiary amine of formula (I).

Preferably, the catalytic bed is supplied with a solution of the reagents at a temperature of 100 to 180° C., or preferably 150 to 175° C.

It is not desirable to aim at a degree of conversion into tertiary amine of formula (I) of more than 50–70% given that it is easy to separate the tertiary amine from the crude reaction mixture. In fact, the reaction rate decreases as the reaction proceeds and the proportion of secondary amine decreases in parallel.

Anyone skilled in the art can also isolate the primary and secondary intermediate amines from the reaction mixture and use them as ammonolysis agents for another reaction. One of the by-products of the reaction is water. This is very easily separated from the reaction product.

Whatever the operating method chosen (continuous or semi-continuous), a gaseous flux will be recovered at the exit from the catalytic bed, containing a mixture of ammonia and water with a certain quantity of unreacted alkyleneglycol monoether.

By simply condensing this gas, a liquid rich in ammonia is obtained from which the water, ammonia and alkyleneglycol monoether can be separated.

The compounds of formula (II) are known. When A and B are identical, the alkyleneglycol monoether can be prepared simply by reacting an alcohol of formula (III):

R—OH  (III)

wherein R is as hereinbefore defined for formula (I), with an alkylene oxide of formula (IV):

(IV)

wherein A is as hereinbefore defined for formula (I).

Of the alkyleneglycol monoethers which may be used, the following may be mentioned:

oxa-3-butanol-1 dioxa-3,6-heptanol-1
trioxa-3,6,9-decanol-1
oxa-3-pentanol-1
dioxa-3,6-octanol-1
trioxa-3,6,9-undecanol-1
oxa-3-hexanol-1
dioxa-3,6-nonanol-1
trioxa-3,6,9-dodecanol-1
oxa-3-heptanol-1
dioxa-3,6-decanol-1
trioxa-3,6,9-tridecanol-1
phenoxy-5-oxa-3-pentanol-1
phenoxy-8-dioxa-3,6-octanol-1
cyclohexoxy-5-oxa-3-pentanol-1
cyclohexoxy-8-dioxa-3,6-octanol-1
nonylphenoxy-5oxa-3-pentanol-1
nonylphenoxy-8-dioxa-3,6-octanol-1
dodecylphenoxy-5-oxa-3-pentanol-1
dodecylphenoxy-8-dioxa-3,6-octanol-1
dioxa-3,6-methyl-4-heptanol-1
dioxa-3,6-dimethyl-2,4-heptanol-1

The tertiary amines of formula (I) prepared by the process according to the invention make it possible to solubilise or increase the solubility of organic or inorganic salts in organic solvents. They are thus useful as sequestering agents but can also be used as catalysts thanks to their excellent complexing properties, or as emulsifiers.

Moreover, unlike the majority of cyclic crown ethers, the amines of formula (I) have low toxicity. These properties mean that these tertiary amines can be used in a variety of fields ranging from the recovery of natural acid gas to the formulation of surfactants and chemical catalysis.

The process according to the invention is particularly suitable for preparing the following tertiary amines:
tris(oxa-3-butyl)amine
tris(dioxa-3,6-heptyl)amine
tris(trioxa-3,6,9-decyl)amine
tris(oxa-3-pentyl)amine
tris(dioxa-3,6-octyl)amine
tris(trioxa-3,6,9-undecyl)amine
tris(oxa-3-hexyl)amine
tris(dioxa-3,6-nonyl)amine
tris(trioxa-3,6,9-dodecyl)amine
tris(oxa-3-heptyl)amine
tris(dioxa-3,6-decyl)amine
tris(trioxa-3,6,9-tridecyl)amine
tris(dioxa-3,6-methyl-4-heptyl)amine
tris(dioxa-3,6-dimethyl-2,4-heptyl)amine
tris(phenoxy-5-oxa-3-pentyl)amine
tris(phenoxy-8-dioxa-3,6-octyl)amine
tris(cyclohexoxy-5-oxa-3-pentyl)amine
tris(cyclohexoxy-8-dioxa-3,6-octyl)amine
tris(nonylphenoxy-5-oxa-3-pentyl)amine
tris(nonylphenoxy-8-dioxa-3,6-octyl)amine
tris(dodecylphenoxy)-5-oxa-3-pentyl)amine
tris(dodecylphenoxy-8dioxa-3,6-octyl)amine
The Examples which follow illustrate the invention.

EXAMPLE 1

Preparation of tris(dioxa-3,6-heptyl)amine by the continuous method:

The catalytic bed used is made up of four tubes arranged in a row, 30 mm in diameter and 3 m long, each filled with 2.6 kg of Ni563 catalyst (sold by Messrs. Procatalyse) in the form of pellets with an equivalent mean diameter of 8 mm.

The catalyst tubes are operated pseudo-adiabatically by a heat-insulating casing and a series of electrical resistors embedded in the insulation so that the temperature of the inner wall of each tube is identical to the temperature of the outer wall.

The solution of reagents is made up of diethyleneglycol monomethylether and contains 6% by weight of ammonia. A solution of reagents preheated to 170° C. is fed in at the top of the catalytic bed at a flow rate of 1.4 kg/h. This procedure is carried out under atmospheric pressure. The solution recovered at the exit from the catalytic bed is a clear yellow liquid containing 59% by weight of tris(dioxa-3,6-heptyl)amine, 3.5% by weight of bis(dioxa-3,6-heptyl)amine and 2.5% by weight of mono(dioxa-3,6-heptyl)amine, the remainder making it up to 100% by weight consisting of unreacted diethyleneglycol monomethylether.

Distillation under reduced pressure (666.5 Pa. i.e. 5 mm of Hg) continued to 240° C. reveals the formation of less than 1% by weight of tar.

EXAMPLE 2

Preparation of tris(dioxa-3,6-heptyl)amine by the continuous method:

This Example is carried out using an identical procedure to Example 1 except that the flow rate of the solution of diethyleneglycol monomethylether through the catalytic bed has been fixed at 2.8 kg/h.

Under these conditions, the following are recovered at the exit from the catalytic bed:
mono(dioxa-3,6-heptyl)amine: 0.3%
bis(dioxa-3,6-heptyl)amine: 15–17%
tris(dioxa-3,6-heptyl)amine: 33–37%
[bis(dioxa-3,6-heptyl)](methoxyethyl)amine: 1.1%
the percentages indicated being percentages by weight based on the total weight of the solution.

The remainder making up 100% by weight consists of unreacted diethyleneglycol monomethylether.

EXAMPLE 3

Preparation of tris(dioxa-3,6-heptyl)amine by the continuous method, in the presence of hydrogen:

In this Example the same procedure is used as in Example 1 except that the catalytic bed is kept permenantly under a hydrogen pressure of 15 atmospheres (1.52 $10^6$ Pa).

Analysis of the solution recovered at the exit from the catalytic bed corresponds exactly to that given in Example 1.

This result confirms that the presence of hydrogen does not alter the reaction product but merely contributes to extending the service life of the catalyst.

EXAMPLE 4

Preparation of tris(dioxa-3,6-heptyl)amine by the continuous method:

In this Example, the ammonolysis agent is bis(dioxa-3,5-heptyl)amine. The catalytic bed described in Example 1 is supplied with a solution of reagents made up of 80% by weight of diethyleneglycol monomethylether and 20% by weight of bis(dioxa-3,6-heptyl)amine, previously heated to 170° C., at a flow rate of 1.4 kg/h.

11

For the rest, the operating conditions are the same as those used in Example 1.

A virtually colourless liquid is recovered at the exit from the catalytic bed, containing, in percent by weight:

bis(dioxa-3,6-heptyl)amine: 2%
tris(dioxa-3,6-heptyl)amine: 26%
[bis(dioxa-3,6-heptyl)](methoxyethyl)amine: 0.5%
diethyleneglycol monomethylether: q.s. ad: 100%

EXAMPLE 5

Preparation of tris(dioxa-3,6-heptyl)amine by the continuous method:

The catalytic bed used consists of two heat insulating tubes arranged in a row, 30 cm in diameter and 12 m long and each filled with 980 kg of reduced Ni 563 catalyst (sold by Procatalyse) in the form of pellets having an equivalent mean diameter of 8 mm.

The solution of reagents is prepared by injecting a flux of 18 kg/h of gaseous ammonia into a liquid current of 284 kg/h of diethyleneglycol monomethylether, previously heated to 170° C., at the top of the catalytic bed.

Within the scope of this example, the work is done under atmospheric pressure.

At the bottom of the first heat insulating tube, a mixture of water vapour and ammonia is eliminated in gaseous form.

The liquid leaving the first heat insulating tube is directed to the entrance to the second heat insulating tube forming part of the catalytic bed.

During stable operation, an outgoing current of 270 kg/h is collected at the bottom of the second tube, comprising (in percent by weight):

tris(dioxa-3,6-heptyl)amine: 60%
bis(dioxa-3,6-heptyl)amine: 4%
[bis(dioxa-3,6-heptyl)][methoxylethyl]amine: 3%
diethyleneglycol monomethylether: q.s. ad 100%.

This liquid can be distilled under reduced pressure (1333 Pa, 10 mm of Hg) without decomposition of the tris(dioxa-3,6-heptyl)amine which is recovered with a purity of 98%.

EXAMPLE 6

Preparation of tris(dioxa-3,6-heptyl)amine by the continuous method:

The catalytic bed in Example 5 is supplied with a current of 284 kg/h of diethyleneglycol monomethylether which has previously been heated to 170° C., into which 18 kg/h of gaseous ammonia is injected at the entrance to the catalytic bed.

150 kg/h of the liquid leaving the catalytic bed are permanently recycled into the entrance to the catalytic bed.

Under stable operation, an outgoing current of 270 kg/h of a mixture having virtually the same composition as Example 5 is obtained.

EXAMPLE 7

Preparation of tris(dioxa-3,6-heptyl)amine by the continuous method

In this Example, the same procedure is used as in Example 5 except that the second heat insulating tube forming the catalytic bed is kept permanently under a hydrogen pressure of 5 atmospheres ($5,065.10^5$ Pa.)

The overall hydrogen consumption is 0.4 m³ TPN/h.

Analysis of the solution leaving the second heat insulating tube corresponds exactly to that obtained in Example 5.

12

What is claimed is:

1. A process for preparing tris(ether-amines) of formula (I)

$$N[A-O-(B-O)_n-R]_3 \quad (I)$$

wherein:

R denotes an alkyl radical having 1 to 24 carbon atoms, a saturated carbocyclic, monocyclic or polycyclic radical having 3 to 10 carbon atoms, an alkyl radical having 1 to 12 carbon atoms and carrying a saturated carbocyclic, monocyclic or polycyclic group having 3 to 10 carbon atoms, an aromatic carbocyclic, monocyclic or polycyclic radial having 6 to 22 carbon atoms; and an alkyl radical having 1 to 12 carbon atoms and carrying an aromatic carbocyclic, monocyclic or polycyclic group having 6 to 18 carbon atoms;

A and B, which may be identical or different, independently denote a straight alkylene chain having 1 to 24 carbon atoms, and n denotes from 0 to 12;

said process comprising reacting, in liquid phase, an alkyleneglycol monoether of formula (II):

$$HO-A-O-(B-O)_n-R \quad (II)$$

wherein R, A, B and n are as hereinbefore defined in formula (I), with an ammonolysis agent comprising ammonia or an ether-amine of formula (I'):

$$H_{3-p}N[A-O-(B-O)_n-R]_p \quad (I')$$

wherein A, B, n and R are as hereinbefore defined for formula (I) and p denotes 1 or 2, at a temperature between 100 and 250° C., by contacting the reagents with a hydrogenation/dehydrogenation catalyst, said contacting being carried out by passing a solution of said reagents, which has previously been heated to a temperature of 100 to 250° C., through a catalytic bed made up of particles of said hydrogenation/dehydrogenation catalyst.

2. The process according to claim 1, wherein:

R denotes $(C_{1-24})$alkyl, cyclohexyl, phenyl or $(C_{1-12})$alkyphenyl;

A and B, which may be identical or different, independently represent a straight $(C_{2-3})$alkylene chain wherein the carbon atoms are optionally substituted by methyl or ethyl; and n denotes an integer between 0 and 4.

3. The process according to claim 1, wherein the solution of said reagents is heated to a temperature of 100 to 180° C. before being passed through said catalytic bed.

4. The process according to claim 1, wherein the particles of catalyst are in the form of porous pellets extruded material or granules or beads or platelets.

5. The process according to claim 1, wherein the catalyst is in the form of particles having an equivalent mean diameter between 3 and 15 mm.

6. The process according to claim 1, wherein the hydrogenation/dehydrogenation catalyst is based on a compound selected from the group consisting of nickel (0), cobalt (0), chromium (0), a nickel oxide, a cobalt oxide, a chloride oxide and the mixtures thereof.

7. The process according to claim 1, wherein the particles of catalyst comprise a hydrogenation/dehydrogenation catalyst supported on an inert carrier, optionally comprises silica, magnesium oxide, alumina, kieselguhr or titanium oxide.

8. The process according to claim 1, wherein the solution of the reagents is passed through the catalytic bed at a spatial velocity, defined as being the ratio of the flow rate of said solution, expressed in tonnes/h, to the total mass of the catalytic bed, expressed in tonnes, of between 0.1 and 0.5 $h^{-1}$.

9. The process according to claim 1, wherein the solution of said reagents comprises 0.5 to 2 moles of the ammonolysis agent per liter of alkyleneglycol monoether (II).

10. The process according to claim 1, wherein the solution of the reagents is prepared by injecting gaseous ammonia into an incoming liquid current of a solution of said alkyleneglycol monoether (II) previously heated to a temperature of 100 to 250° C., at the entrance to the catalytic bed.

11. The process according to claim 1, wherein it is carried out continuously.

12. The process according to claim 1, wherein some of the solution leaving the catalytic bed is recycled into the entrance to said catalytic bed or into an intermediate position located between the entrance and the exit of said catalytic bed.

13. The process according to claim 1, wherein the process is carried out semi-continuously by carrying out steps comprising:

(i) continuously supplying the catalytic bed with a solution of the reagents, previously heated to a temperature of 100 to 250° C., and recovering the treated solution at the exit from said catalytic bed in a recovery tank until a concentration of tris(ether-amine) of formula (I) of 0.5 to 2 mol/l is obtained in the recovery tank, then (ii) recycling the solution recovered in said recovery tank into the catalytic bed; and passing it through the catalytic bed once more; and (iii) repeating the recycling step of the solution recovered in the recovery tank, at the end of step (ii), into the catalytic bed as many times as is necessary to obtain the desired degree of conversion into tertiary amine of formula (I).

14. The process according to claim 1, wherein the catalytic bed is maintained in a vertical position, the solution of the reagents circulating from top to bottom.

15. The process according to claim 1, wherein the ammonia is reacted with diethyleneglycol monomethylether in order to prepare tris(dioxa-3,6-heptyl)amine.

* * * * *